United States Patent
McIntire et al.

(10) Patent No.: US 9,170,264 B2
(45) Date of Patent: Oct. 27, 2015

(54) METHODS OF MONITORING FOR ADHERENCE TO ARIPIPRAZOLE THERAPY

(71) Applicant: Ameritox, Ltd., Baltimore, MD (US)

(72) Inventors: Gregory L. McIntire, Greensboro, NC (US); Ayodele Morris, Midland, TX (US)

(73) Assignee: Ameritox, Ltd., Baltimore, MD (US)

( * ) Notice: Subject to any disclaimer, the term of this patent is extended or adjusted under 35 U.S.C. 154(b) by 0 days.

(21) Appl. No.: 14/213,392

(22) Filed: Mar. 14, 2014

(65) Prior Publication Data

US 2014/0284467 A1     Sep. 25, 2014

Related U.S. Application Data

(60) Provisional application No. 61/798,443, filed on Mar. 15, 2013.

(51) Int. Cl.
| | |
|---|---|
| *G01N 33/70* | (2006.01) |
| *G01N 30/72* | (2006.01) |
| *G01N 33/68* | (2006.01) |

(52) U.S. Cl.
CPC ............ *G01N 33/6893* (2013.01); *G01N 30/72* (2013.01); *G01N 33/70* (2013.01); *G01N 2800/30* (2013.01); *G01N 2800/302* (2013.01); *G01N 2800/52* (2013.01); *Y10T 436/147777* (2015.01); *Y10T 436/24* (2015.01)

(58) Field of Classification Search
CPC .......... G01N 2800/00; G01N 2800/30; G01N 2800/302; G01N 2800/52; G01N 33/68; G01N 33/6893; G01N 33/70; G01N 33/94; G01N 33/9466; G01N 30/62; G01N 30/72; Y10T 436/145555; Y10T 436/147777; Y10T 436/24
USPC .................. 436/63, 96, 98, 161, 173; 435/29; 250/282; 514/17.5, 17.6; 424/400
See application file for complete search history.

(56) References Cited

U.S. PATENT DOCUMENTS

| | | | |
|---|---|---|---|
| 2010/0004262 A1* | 1/2010 | Wilding et al. | 514/253.07 |
| 2011/0195520 A1* | 8/2011 | Leider et al. | 436/501 |
| 2012/0208718 A1* | 8/2012 | Gault et al. | 506/9 |

OTHER PUBLICATIONS

Tsai et al. Journal of the Chinese Medical Association, vol. 74, 2011, pp. 267-271.*
Dretchen et al. Journal of Phamacology and Clinical Toxicology, vol. 1(2), 1014, Dec. 30, 2013, pp. 1-4.*

* cited by examiner

*Primary Examiner* — Maureen Wallenhorst
(74) *Attorney, Agent, or Firm* — Perkins Coie LLP (57) ABSTRACT

Methods for helping to monitor subject adherence with a prescribed antipsychotic drug treatment regimen are disclosed.

35 Claims, 1 Drawing Sheet

METHODS OF MONITORING FOR ADHERENCE TO ARIPIPRAZOLE THERAPY

PRIORITY CLAIM

This application claims priority to U.S. provisional patent application Ser. No. 61/798,443, filed on Mar. 15, 2013, the entire contents of which are incorporated herein by reference and relied upon.

FIELD

The present invention provides methods for helping monitor patient adherence to aripiprazole therapy in the treatment of Schizophrenia and other Mental Health Disorders.

SUMMARY

In various embodiments, the present invention provides methods for helping monitor patient adherence to aripiprazole therapy in the treatment of Schizophrenia and other Mental Health Disorders. In one embodiment, the method involves the use of OPC3373 as a biomarker in urine.

These and other embodiments of the invention will be disclosed in further detail herein below.

DETAILED DESCRIPTION

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about" Also, the disclosure of ranges is intended as a continuous range including every value between the minimum and maximum values recited as well as any ranges that can be formed by such values. Also disclosed herein are any and all ratios (and ranges of any such ratios) that can be formed by dividing a disclosed numeric value into any other disclosed numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present invention.

Aripiprazole (Abilify®, Abilitat™) is an atypical antipsychotic prescribed for the treatment of schizophrenia. Adherence has been shown, for example by Velligan, et al., (*Psychiatric Services,* 54:665, 667 (2003)), to be particularly low in patients with schizophrenia. Urine drug testing has been employed by behavioral health clinicians such as described by Baselt, *Disposition of Toxic Drugs and Chemicals in Man* (2004) to monitor patient adherence through analysis of aripiprazole itself and the major plasma metabolite, dehydroaripiprazole. Typical dosing of aripiprazole is 2-30 mg/day. It is well absorbed after oral administration with an oral bioavailability of 87%. The mean elimination half-life is 75 hours. Steady state serum concentrations for aripiprazole are achieved after two weeks of dosing.

Figure 1:
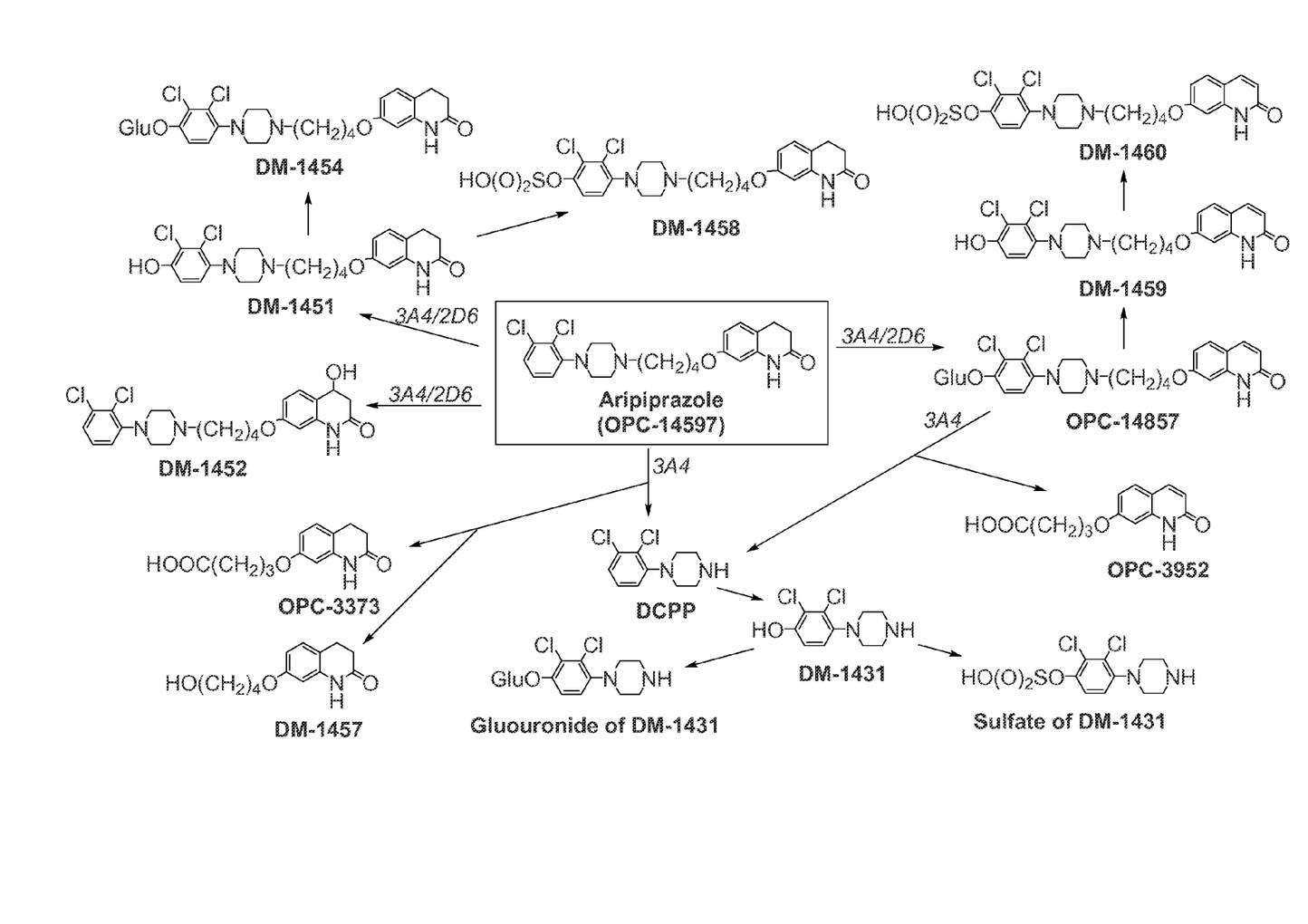
FIG. 1 depicts a proposed metabolic pathway for aripiprazole.

Aripiprazole is metabolized in the liver primarily by dehydrogenation and hydroxylation by both CYP2D6 and CYP3A4 and by N-dealkylation by CYP3A4. The dehydrogenation biotransformation pathway produces the pharmacologically active metabolite dehydroaripiprazole. N-dealkylation splits aripiprazole into metabolites, OPC3373 and DCPP. OPC3373 is an acid product with a quinoline moiety and butyl side chain. Hydroxylation produces metabolites, DM-1452 and DM-1451. Secondary biotransformations include N-dealkylation, hydroxylation, glucuronidation and sulfation. The proposed metabolic pathway for aripiprazole is shown in FIG. 1. In plasma, aripiprazole is the predominant species, representing 57% of a dose, followed by dehydroaripiprazole at 20%, as the major metabolite and OPC-3373 as the second major metabolite at 2%. Aripiprazole is eliminated by renal and biliary routes in humans. Less than 1% of an oral dose is excreted as unchanged aripiprazole in urine, with 8-18% in faeces. The N-dealkylation metabolites OPC3373 and DCPP and related metabolites are excreted predominantly in urine. Baselt, supra, reports that OPC3373 is the major urinary metabolite, with 19% being recovered from a dose. It is therefore an ideal biomarker for monitoring adherence to aripiprazole by urine drug testing. The larger hydroxylation and dehydrogenation metabolites are excreted predominantly in faeces.

In one embodiment, the present disclosure provides a method for monitoring aripiprazole therapy in a subject. In some embodiments, the method comprises identifying a subject who is prescribed aripiprazole therapy, measuring a concentration of OPC3373 in urine of the subject, and identifying the subject as non-adherent to aripiprazole therapy if the concentration of OPC3373 is less than a predetermined level, and as adherent to aripiprazole therapy if the concentration of OPC3373 is greater than the predetermined level. In some embodiments, the method further comprises counseling the subject on dangers of non-adherence to aripiprazole therapy if the subject is identified as non-adherent. In some embodiments, the predetermined level is 25 ng/mL.

In some embodiments, the aripiprazole therapy includes prescribing to the subject and/or administering to the subject aripiprazole in an amount selected from the group consisting of: 2 mg/day, 5 mg/day, 10 mg/day, 15 mg/day, 20 mg/day, or 30 mg/day.

In some embodiments, the method further comprises measuring a concentration of aripiprazole in urine of the subject, and identifying the subject as non-adherent if the concentrations of aripiprazole and OPC3373 are both less than predetermined levels of aripiprazole and OPC3373, respectively. In some embodiments the predetermined level of aripiprazole is 5 ng/mL. In some embodiments, the predetermined level of OPC3373 is 25 ng/mL.

In some embodiments, the method further comprises measuring a concentration of dehydroaripiprazole in urine of the subject, and identifying the subject as non-adherent if the concentrations of dehydroaripiprazole and OPC3373 are both less than predetermined levels of dehydroaripiprazole and OPC3373, respectively. In some embodiments, the predetermined level of dehydroaripiprazole is 5 ng/mL. In some embodiments, the predetermined level of OPC3373 is 25 ng/mL.

In some embodiments, the method comprises measuring concentrations of aripiprazole, dehydroaripiprazole and OPC3373 in urine of the subject, and identifying the subject as non-adherent if the concentrations of aripiprazole, dehydroaripiprazole and OPC3373 are each less than predetermined levels of aripiprazole, dehydroaripiprazole and OPC3373, respectively. In some embodiments, the predetermined level of aripiprazole is 5 ng/mL. In some embodiments, the predetermined level of dehydroaripiprazole is 5 ng/mL. In some embodiments, the predetermined level of OPC3373 is 25 ng/mL.

In some embodiments, the method comprises measuring concentrations of aripiprazole, dehydroaripiprazole and OPC3373 in urine of the subject, and identifying the subject as non-adherent if the concentrations of any one, any two, or all three of aripiprazole, dehydroaripiprazole and OPC3373 are less than predetermined levels of aripiprazole, dehydroaripiprazole and OPC3373, respectively. In some embodiments, the predetermined level of aripiprazole is 0.05 ng/mL. In some embodiments, the predetermined level of dehydroaripiprazole is 0.05 ng/mL. In some embodiments, the predetermined level of OPC3373 is 0.25 ng/mL.

The concentration of any analyte described in the present disclosure may be determined (e.g., measured) by any suitable quantification method. In some embodiments, the concentration of an analyte (e.g., aripiprazole, dehydroaripiprazole, and/or OPC3373) is measured by tandem liquid chromatography-mass spectrometry-mass spectrometry ("LC/MSMS"). In some embodiments, the concentration of an analyte (e.g., aripiprazole, dehydroaripiprazole, and/or OPC3373) is measured by tandem liquid chromatography-High Resolution mass spectrometry (Time of Flight (TOF)) ("LC/MS(TOF)"). In some embodiments, the concentration of an analyte (e.g., aripiprazole, dehydroaripiprazole, and/or OPC3373) is measured by direct injection mass spectrometry-mass spectrometry ("LC/MSMS") e.g., such systems as RapidFire™ (Agilent) or Laser Diode Thermal Desorption ("LDTD") (Phytronix) to introduce samples into the mass spectrometer; either triple quadrupole (i.e., MSMS) or exact mass (i.e., Time of Flight, Orbitrap, etc.) instruments In some embodiments, the method further comprises measuring a creatinine level in urine of the subject and normalizing the OPC3373 concentration as a function of the creatinine concentration, wherein the predetermined level comprises a ratio of the OPC3373 concentration to the creatinine concentration.

In some embodiments, the method further comprises measuring a specific gravity value of the urine of the subject, and normalizing the OPC3373 concentration as a function of the specific gravity value, wherein the predetermined level comprises a ratio of the OPC3373 concentration to the specific gravity value.

In some embodiments, the method further comprises measuring a creatinine level in urine of the subject and normalizing the aripiprazole concentration as a function of the creatinine concentration, wherein the predetermined level comprises a ratio of the aripiprazole concentration to the creatinine concentration.

In some embodiments, the method further comprises measuring a specific gravity value of the urine of the subject, and normalizing the aripiprazole concentration as a function of the specific gravity value, wherein the predetermined level comprises a ratio of the aripiprazole concentration to the specific gravity value.

In some embodiments, the method further comprises measuring a creatinine level in urine of the subject and normalizing the dehydroaripiprazole concentration as a function of the creatinine concentration, wherein the predetermined level of the dehydroaripiprazole comprises a ratio of the dehydroaripiprazole concentration to the creatinine concentration.

In some embodiments, the method further comprises measuring a specific gravity value of the urine of the subject, and normalizing the dehydroaripiprazole concentration as a function of the specific gravity value, wherein the predetermined level of the dehydroaripiprazole comprises a ratio of the dehydroaripiprazole concentration to the specific gravity value.

In some embodiments, the method further comprises measuring a creatinine value in urine of the subject and a specific gravity value of urine of the subject and normalizing the aripiprazole, dehydroaripiprazole and/or OPC3373 ("analyte") concentration(s) as a function of the creatinine and specific gravity values, wherein the predetermined level of the analyte comprises a ratio of the analyte concentration to the creatinine and specific gravity values.

In some embodiments, the method further comprises generating a normal distribution of OPC3373 in aripiprazole subjects using the log(OPC3373 concentration) from a plurality of measured OPC3373 concentrations in urine from a plurality of subjects, for example a plurality of subjects known to be adherent to aripiprazole therapy. In some embodiments, the method further comprises identifying a concentration of OPC3373 in urine of a second (test) subject as normal if it falls within the normal distribution (e.g., within 2 standard deviations of the mean) of OPC3373 of the plurality of known adherent aripiprazole subjects, and/or identifying the concentration of OPC3373 in urine of the second (test) subject as not normal if it falls outside the normal distribution of OPC3373 in the plurality of known adherent aripiprazole subjects. In some embodiments, the concentration of OPC3373 in urine of the second (test) subject is incorporated into the distribution model, that is, the OPC3373 concentration from the second (test) subject is used along with the OPC3373 concentrations from the plurality of aripiprazole subjects to generate a second, refined normal distribution of OPC3373 in aripiprazole subjects.

In some embodiments, the method further comprises generating a normal distribution of aripiprazole in aripiprazole subjects using the log(aripiprazole concentration) from a plurality of measured aripiprazole concentrations in urine from a plurality of subjects, for example a plurality of subjects known to be adherent to aripiprazole therapy. In some embodiments, the method further comprises identifying a concentration of aripiprazole in urine of a second (test) subject as normal if it falls within the normal distribution (e.g., within 2 standard deviations of the mean) of aripiprazole of the plurality of known adherent aripiprazole subjects, and/or identifying the concentration of aripiprazole in urine of the second (test) subject as not normal if it falls outside the normal distribution of aripiprazole in the plurality of known adherent aripiprazole subjects. In some embodiments, the concentration of aripiprazole in urine of the second (test) subject is incorporated into the distribution model, that is, the aripiprazole concentration from the second (test) subject is used along with the aripiprazole concentrations from the plurality of aripiprazole subjects to generate a second, refined normal distribution of aripiprazole in aripiprazole subjects.

In some embodiments, the method further comprises generating a normal distribution of dehydroaripiprazole in aripiprazole subjects using the log(dehydroaripiprazole concentration) from a plurality of measured dehydroaripiprazole concentrations in urine from a plurality of subjects, for example a plurality of subjects known to be adherent to aripiprazole therapy. In some embodiments, the method further comprises identifying a concentration of dehydroaripiprazole in urine of a second (test) subject as normal if it falls within the normal distribution (e.g., within 2 standard deviations of the mean) of dehydroaripiprazole of the plurality of known adherent aripiprazole subjects, and/or identifying the concentration of dehydroaripiprazole in urine of the second (test) subject as not normal if it falls outside the normal distribution of dehydroaripiprazole in the plurality of known adherent aripiprazole subjects. In some embodiments, the concentration of dehydroaripiprazole in urine of the second (test) subject is incorporated into the distribution model, that is, the dehydroaripiprazole concentration from the second (test) subject is used along with the dehydroaripiprazole concentrations from the plurality of aripiprazole subjects to generate a second, refined normal distribution of dehydroaripiprazole in aripiprazole subjects.

Any method disclosed herein may additionally comprise counseling a subject on dangers of non-adherence to aripiprazole therapy if the subject is identified as non-adherent.

In some embodiments, the method further comprises modifying the subject's prescribed dose of aripiprazole if the subject is identified as being non-adherent with the prescribed aripiprazole therapy. In some embodiments, the method further comprises discontinuing aripiprazole therapy in the subject if the subject is identified as being non-adherent. In some embodiments, the method further comprises replacing aripiprazole therapy in the subject with a new therapeutic regimen if the subject is identified as being non-adherent. In some embodiments, the method further comprises discontinuing aripiprazole therapy in the subject and increasing a dose of a second anti-psychotic drug in the subject. In some embodiments, the method further comprises maintaining (e.g., not modifying or not significantly modifying) the subject's prescribed dose of aripiprazole if the subject is identified as being adherent with the prescribed aripiprazole therapy.

In some embodiments, the method further comprises determining a clinical effect of a subject's aripiprazole therapy, the method comprising identifying a subject who is prescribed aripiprazole therapy, measuring a concentration of one or more of OPC3373, aripiprazole, and dehydroaripiprazole in urine of the subject, identifying the subject as adherent to aripiprazole therapy if the concentration of OPC3373, aripiprazole and/or dehydroaripiprazole falls within a normal distribution of OPC3373, aripiprazole and/or dehydroaripiprazole (respectively), identifying an inadequate clinical response to the prescribed aripiprazole therapy in the subject, and replacing the prescribed aripiprazole therapy with a different anti-psychotic drug therapy.

EXAMPLES

Example 1

The appearance of OPC3373 (4-[(2-Oxo-1,2,3,4-tetrahydro-7-quinolinyl)oxy]butanoic acid, BMS-337047) as the major aripiprazole metabolite in the urine can be used to help monitor patient adherence to aripiprazole therapy. While analysis of both aripiprazole and the plasma metabolite, dehydroaripiprazole, can be used to monitor patient adherence, the relatively low levels of these molecules in the urine frequently results in "false negatives" in patients known to be taking aripiprazole. As shown in Table 1, the level of OPC3373 in the urine exceeds that of both aripiprazole and the major plasma metabolite, dehydroaripiprazole by as much as 5-120× and as much as 200× in normally metabolizing humans who are known to be taking chronic doses of aripiprazole.

TABLE 1

Levels of OPC3373 in Human Urine Relative to Aripiprazole and Dehydroaripiprazole (ng/mL)

| Sample ID | OPC3373 LOQ = 100 ng/mL | Dehydroaripiprazole LOQ = 5 ng/mL | Aripiprazole LOQ = 5 ng/mL |
|---|---|---|---|
| Specimen 1 | <100.0 | 8.8 | 5.0 |
| Specimen 2 | 5353.4 | 56.1 | 39.5 |
| Specimen 3 | 285.4 | <5.0 | 9.5 |
| Specimen 4 | <100.0 | <5.0 | <5.0 |
| Specimen 5 | <100.0 | 5.1 | <5.0 |
| Specimen 6 | 159.7 | 14.1 | 32.4 |
| Specimen 7 | 877.6 | 0.0 | 9.7 |
| Specimen 8 | 868.9 | 17.8 | 53.3 |
| Specimen 9 | 628.9 | 20.1 | 84.9 |
| Specimen 10 | 136.7 | 5.1 | 38.7 |
| Specimen 11 | 108.0 | <5.0 | <5.0 |
| Specimen 12 | <100.0 | 0.0 | <5.0 |
| Specimen 13 | 1203.6 | <5.0 | 10 |
| Specimen 14 | 607.7 | <5.0 | <5.0 |
| Specimen 15 | 180.2 | 0.0 | 0.0 |
| Specimen 16 | 819.4 | 5.9 | 17.4 |
| Specimen 17 | <100.0 | 0.0 | 0.0 |
| Specimen 18 | 657.3 | <5.0 | <5.0 |
| Specimen 19 | <100.0 | <5.0 | <5.0 |
| Specimen 20 | <100.0 | 0.0 | <5.0 |
| Specimen 21 | <100.0 | 0 | <5.0 |
| Specimen 22 | 2149.2 | 15.8 | 17.9 |
| Range | 10*-1500 ng/mL | 5-75 ng/mL | 5-100 ng/mL |
| % NEG at 100/5/5 ng/mL Cutoff | 27.2 | | |
| % POS with OPC3373 only | 22.7 | | |

*Below LOQ

Thus, for the purposes of helping to monitor patients for adherence to aripiprazole therapy, testing of the metabolite, OPC3373, provides a greater level of sensitivity and therefore the ability to identify aripiprazole positive patients when commonly available compounds including aripiprazole and dehydroaripiprazole are not reflective of adherent patients in as many as 50% of the patient positive population. Inasmuch as aripiprazole is used for the treatment of psychotic individuals, it is important to be able to identify drug positive patients at very low levels.

Example 2

An additional set of aripiprazole positive patients was monitored for levels of aripiprazole, dehyrdroaripiprazole, and OPC3373 in their urine. Table 2 details the results of testing on these subjects, and demonstrates that OPC3373 is a much better biomarker for adherence to aripiprazole therapy than the parent compound or the primary plasma metabolite, dehydroaripiprazole. Sample number 3 in Table 2 demonstrated very low levels of creatinine and as is well known in the industry may have been severely diluted such that the aripiprazole metabolite, OPC3373, was below levels of quantitation.

For these data the Lower Level of Quantitation (LLOQ) for the analytes in question were:

Aripiprazole: 5 ng/mL

Dehydroaripiprazole: 5 ng/mL

OPC3373: 25 ng/mL

These analyses were completed using LC/MSMS.

TABLE 2

Results from Testing Urine from Aripiprazole Positive Patients in a Controlled Study

| # | Dose | Sample ID | Specimen Validity Results | | | Abilify Urine Results (ng/mL) | | | Comments |
|---|---|---|---|---|---|---|---|---|---|
| | | | pH | Creatinine | Specific Gravity | OPC3373 | Dehydro-aripiprazole | Aripiprazole | |
| 1 | 5 mg q day | 001CK | 5.3 | 97.3 | 1.015 | 410.7 | 5.2 | 19.4 | |
| 2 | 5 mg q day | 002CF | 6.6 | 366.1 | 1.031 | 2338.8 | 6.4 | 11.6 | |
| 3 | 5 mg q day | 003MS | 4.8 | 9.0 | 1.004 | 0 | 0 | 0 | Peaks detected, but less than LOD/LOQ |
| 4 | 5 mg q day | 004TJ | 5.2 | 172.7 | 1.023 | 175.0 | 0 | 11.1 | Peak detected, but less than LOD/LOQ |
| 5 | 5 mg q day | 006NT | 5.5 | 182.5 | 1.028 | 1213.6 | 6.5 | 22.3 | |
| 6 | 5 mg q day | 007ET | 5.0 | 87.7 | 1.015 | 79.0 | 0 | 9.4 | Peak detected, but less than LOD/LOQ |

Example 3

The urine of 5 patients who were prescribed 30 mg of Abilify® (aripiprazole) was tested for compliance over 5 days (Table 3). The data in Table 4 demonstrate the "normal" nature of the sample validity criteria (i.e., pH, specific gravity, and creatinine). The preponderance of OPC3373 in the urine as the major metabolic urine compound is clearly demonstrated in Table 3. Assuming 15 opportunities to determine the patient to be either positive or negative for Abilify® dosing, the use of OPC3373 resulted in 100% correct identification of those taking the prescribed medicine. Without OPC3373, only 93% were determined to be positive with one patient either having stopped taking their medicine between day 4 and 5 or just being below the reporting cutoffs for both aripiprazole and dehydroaripiprazole. Thus, use of OPC3373 as a urine biomarker even at this relatively high dose adds value to compliance monitoring for Abilify®.

TABLE 3

Test Results from Patients Prescribed 30 mg/day Abilify®

| Sub | Day | pH | Creatinine (mg/dL) | Specific Gravity | Aripiprazole | Dehydro-aripiprazole | OPC3373 |
|---|---|---|---|---|---|---|---|
| A | 1 | 5.1 | 152.6 | 1.013 | 45.7 | 14.1 | 981.5 |
| | 4 | 5.6 | 227.6 | 1.015 | 34.0 | 16.6 | 1935.4 |
| | 5 | 5.6 | 293.8 | 1.016 | 55.5 | 28.1 | 2248.8 |
| B | 1 | 7.1 | 38.7 | 1.006 | 16.5 | 11.5 | 371.3 |
| | 4 | 5.4 | 55.9 | 1.006 | 16.9 | 14.1 | 515.6 |
| | 5 | 5.0 | 34.4 | 1.004 | 0 | 0 | 260.1 |
| C | 1 | 5.8 | 220.3 | 1.015 | 30.8 | 29.2 | 3050.9 |
| | 4 | 5.5 | 254.6 | 1.018 | 53.4 | 84.8 | 3128.9 |
| | 5 | 7.0 | 142.1 | 1.011 | 12.6 | 17.0 | 1601.0 |
| D | 1 | 6.7 | 126.9 | 1.010 | 0 | 6.8 | 1688.0 |
| | 4 | 7.3 | 243.1 | 1.011 | 0 | 11.0 | 4160.0 |
| | 5 | 6.1 | 186.3 | 1.012 | 10.6 | 8.9 | 2417.9 |
| E | 1 | 6.5 | 188.5 | 1.013 | 83.3 | 56.9 | 4383.3 |
| | 4 | 5.0 | 39.4 | 1.005 | 113.0 | 36.3 | 481.0 |
| | 5 | 5.4 | 177.1 | 1.019 | 199.8 | 89.7 | 3141 |

TABLE 4

Sample Validity and Urine Results Summary at 30 mg/day

| | pH | Creatinine (mg/dL) | Specific Gravity | Aripiprazole (ng/mL) | Dehydro-aripiprazole (ng/mL) | OPC3373 (ng/mL) |
|---|---|---|---|---|---|---|
| Avg | 5.94 | 158.75 | 1.01 | 44.81 | 28.33 | 2024.31 |
| Std Dev | 0.79 | 84.97 | 0.00 | 53.76 | 27.69 | 1356.01 |
| n | 15.00 | | | | | |
| Max | 7.30 | 293.80 | 1.02 | 199.80 | 89.70 | 4383.30 |
| Min | 5.00 | 34.40 | 1.00 | 0.00 | 0.00 | 260.10 |

Example 4

The urine of 22 patients who were prescribed 20 mg of Ability (e.g., aripiprazole) was tested for compliance over 5 days (Table 5). The data in Table 6 demonstrate the "normal" nature of the sample validity criteria (i.e., pH, specific gravity, and creatinine). The preponderance of OPC3373 in the urine as the major metabolic urine compound is clearly demonstrated in Table 5. Assuming 66 opportunities to determine the patient to be either positive or negative for Abilify® dosing, the use of OPC3373 resulted in 100% correct identification of those taking the prescribed medicine. Without OPC3373, only 85% were determined to be positive with patients just being below the reporting cutoffs for both aripiprazole and dehydroaripiprazole. Thus, use of OPC3373 as a urine biomarker even at this relatively high dose adds value to compliance monitoring for Abilify®.

TABLE 5

Test Results from Patients Prescribed 20 mg/day Abilify®

| Sub. | pH | Creatinine (mg/dL) | Specific Gravity | Aripiprazole | Dehydro-aripiprazole | OPC3373 |
|---|---|---|---|---|---|---|
| A | 5.5 | 55.7 | 1.005 | 28.5 | 14.6 | 626.3 |
| | 7.1 | 60.3 | 1.007 | 9.9 | 8.7 | 696.2 |
| | 6.2 | 57.2 | 1.008 | 11.1 | 7.1 | 883.5 |
| B | 5.2 | 69.1 | 1.037 | 6.5 | 7.2 | 213.7 |
| | 5.5 | 59.0 | 1.037 | 6.1 | 7.7 | 187.7 |
| | 5.2 | 109.8 | 1.013 | 9.6 | 16.9 | 487.7 |

TABLE 5-continued

Test Results from Patients Prescribed 20 mg/day Abilify ®

| Sub. | pH | Creatinine (mg/dL) | Specific Gravity | Aripiprazole | Dehydroaripiprazole | OPC3373 |
|---|---|---|---|---|---|---|
| C | 5.0 | 67.1 | 1.017 | 36.7 | 16.5 | 865.5 |
|   | 5.5 | 124.7 | 1.016 | 40.5 | 17.9 | 1561.5 |
|   | 5.0 | 56.8 | 1.005 | 27.6 | 12.2 | 744.8 |
| D | 6.5 | 219.2 | 1.015 | 21.6 | 20.5 | 1648.5 |
|   | 5.8 | 249.0 | 1.017 | 57.6 | 91.4 | 1287.4 |
|   | 5.5 | 195.8 | 1.013 | 50.4 | 71.3 | 710 |
| E | 8.9 | 314.9 | 0.993* | 17.7 | 17.2 | 1442.2 |
|   | 8.9 | 199.9 | 0.986* | 10.9 | 15.3 | 1379.3 |
|   | 8.8 | 180.5 | 0.998* | 0 | 7.3 | 1248.6 |
| F | 5.7 | 129.3 | 1.008 | 7.1 | 6.2 | 1087.2 |
|   | 5.3 | 80.3 | 1.008 | 14.3 | 8.5 | 464.5 |
|   | 5.6 | 59.1 | 1.007 | 6.9 | 0 | 435.6 |
| G | 6.0 | 87.3 | 1.011 | 16.4 | 11.4 | 1248.9 |
|   | 5.9 | 39.7 | 1.006 | 13.6 | 5.6 | 448.1 |
|   | 6.8 | 90.2 | 1.007 | 5.2 | 6.6 | 1174.0 |
| H | 5.5 | 37.9 | 1.006 | 16.2 | 0 | 280.1 |
|   | 6.8 | 32.8 | 1.004 | 0 | 0 | 230.4 |
|   | 7.1 | 17.2* | 1.003 | 0 | 0 | 100.8 |
| I | 5.6 | 264.1 | 1.015 | 36.6 | 25.5 | 4199.1 |
|   | 6.6 | 147.4 | 1.013 | 5.6 | 7.2 | 2524.6 |
|   | 6.3 | 141.8 | 1.013 | 14.3 | 12.6 | 2008.2 |
| J | 6.4 | 46.3 | 1.005 | 10.4 | 0 | 416.1 |
|   | 7.6 | 99.7 | 1.014 | 16.1 | 7.0 | 1527.5 |
|   | 5.9 | 149.2 | 1.017 | 24.1 | 11.8 | 2191.8 |
| K | 5.5 | 189.0 | 1.013 | 58.7 | 27.4 | 1649.1 |
|   | 5.2 | 75.5 | 1.009 | 42.4 | 16.6 | 556.6 |
|   | 6.0 | 162.2 | 1.017 | 51.1 | 32.5 | 1516.8 |
| L | 5.1 | 133.3 | 1.016 | 84.9 | 34.2 | 2667.1 |
|   | 7.1 | 143.4 | 1.013 | 0 | 7.5 | 2225.5 |
|   | 6.2 | 199.0 | 1.016 | 25.0 | 16.5 | 2447.1 |
| M | 5.7 | 22.0 | 1.002* | 6.9 | 0 | 267.1 |
|   | 5.3 | 14.7* | 1.003 | 5.2 | 0 | 202.1 |
|   | 5.5 | 15.0* | 1.002* | 0 | 0 | 167 |
| N | 5.4 | 226.1 | 1.011 | 5.6 | 6.5 | 284.2 |
|   | 5.5 | 364.9 | 1.019 | 21.5 | 13.9 | 1007.7 |
|   | 5.3 | 354.7 | 1.018 | 26.7 | 18.0 | 913.8 |
| O | 5.8 | 172.6 | 1.016 | 36.5 | 9.9 | 4092.7 |
|   | 5.9 | 104.4 | 1.012 | 16.2 | 5.0 | 1240.3 |
|   | 5.8 | 273.5 | 1.017 | 41.3 | 12.4 | 4927.7 |
| P | 6.5 | 41.6 | 1.008 | 13.8 | 0 | 700.7 |
|   | 5.1 | 69.4 | 1.012 | 49.3 | 11.1 | 1499.6 |
|   | 6.3 | 53.3 | 1.009 | 29.7 | 6.9 | 765.3 |
| Q | 5.4 | 181.1 | 1.019 | 64.0 | 12.8 | 4156.0 |
|   | 5.4 | 50.6 | 1.007 | 21.3 | 10.3 | 1697.6 |
|   | 7.1 | 59.1 | 1.010 | 0 | 0 | 2210.8 |
| R | 6.8 | 26.8 | 1.003 | 0 | 0 | 497.3 |
|   | 7.0 | 25.6 | 1.003 | 5.3 | 0 | 406.3 |
|   | 7.0 | 25.7 | 1.003 | 0 | 0 | 570.0 |
| S | 5.2 | 317.2 | 1.020 | 87.2 | 27.7 | 2562.9 |
|   | 5.2 | 324.2 | 1.021 | 75.0 | 25.7 | 2702.1 |
|   | 5.3 | 350.4 | 1.021 | 137.6 | 64.6 | 4591.0 |
| T | 5.4 | 52.4 | 1.008 | 28.3 | 6.2 | 732.1 |
|   | 6.6 | 48.8 | 1.007 | 14.9 | 0 | 296.2 |
|   | 7.1 | 59.1 | 1.008 | 0 | 0 | 442.5 |
| U | 5.4 | 112.6 | 1.011 | 7.8 | 5.5 | 182 |
|   | 7.0 | 109.6 | 1.005 | 0 | 0 | 160.4 |
|   | 7.3 | 27.6 | 1.005 | 0 | 0 | 38.2 |
| V | 6.8 | 17.7 | 1.003 | 0 | 0 | 91.4 |
|   | 5.4 | 60.0 | 1.008 | 8.4 | 0 | 469.0 |
|   | 5.3 | 96.3 | 1.012 | 18.8 | 6.6 | 1128.1 |

*Measurement is below limits for specimen validity parameter; specimen still valid.

TABLE 6

Sample Validity and Urine Results Summary at 20 mg/day Abilify ®

|  | pH | Creatinine (mg/dL) | Specific Gravity | Aripiprazole | Dehydroaripiprazole | OPC3373 |
|---|---|---|---|---|---|---|
| Avg | 6.08 | 121.22 | 1.01 | 22.80 | 12.30 | 1248.25 |
| Std Dev | 0.93 | 95.66 | 0.01 | 25.72 | 16.58 | 1163.41 |
| n | 66.00 |  |  |  |  |  |
| Max | 8.90 | 364.90 | 1.04 | 137.60 | 91.40 | 4927.70 |
| Min | 5.00 | 14.70 | 0.99 | 0.00 | 0.00 | 38.20 |

Example 5

The urine of 23 patients who were prescribed 15 mg of Abilify® (aripiprazole) was tested for compliance over 5 days (Table 7). The data in Table 8 demonstrate the "normal" nature of the sample validity criteria (i.e., pH, specific gravity, and creatinine). The preponderance of OPC3373 in the urine as the major metabolic urine compound is clearly demonstrated in Table 7. Assuming 69 opportunities to determine the patient to be either positive or negative for Abilify® dosing, the use of OPC3373 resulted in 99% correct identification of those taking the prescribed medicine. Without OPC3373, only 78% were determined to be positive with patients just being below the reporting cutoffs for both aripiprazole and dehydroaripiprazole. Notably, subject N demonstrated very dilute urine (i.e., creatinine <10 mg/dL) and yet, the level of OPC3373 confirmed that subject's adherence to aripiprazole therapy. Thus, use of OPC3373 as a urine biomarker at this dose adds value to compliance monitoring for Abilify®.

TABLE 7

Test Results from Patients Prescribed 15 mg/day Abilify ®

| Sub | Day | pH | Creatinine (mg/dL) | Specific Gravity | Aripiprazole | Dehydroaripiprazole | OPC3373 |
|---|---|---|---|---|---|---|---|
| A | 1 | 7.0 | 64.7 | 1.008 | 14.6 | 6.6 | 586.4 |
|   | 4 | 7.6 | 81.0 | 1.013 | 19.0 | 8.0 | 586.3 |
|   | 5 | 6.1 | 38.6 | 1.007 | 9.6 | 0 | 333.4 |
| B | 1 | 5.3 | 242.3 | 1.025 | 52.2 | 27.9 | 1273.6 |
|   | 4 | 5.4 | 225.2 | 1.024 | 31.7 | 16.8 | 1401.6 |
|   | 5 | 5.4 | 260.1 | 1.027 | 22.8 | 12.8 | 1723.1 |
| C | 1 | 7.8 | 36.9 | 1.007 | 0 | 0 | 347.3 |
|   | 4 | 5.6 | 35.8 | 1.006 | 19.5 | 7.4 | 353.5 |
|   | 5 | 7.1 | 11.0* | 1.002* | 0 | 0 | 83.6 |
| D | 1 | 7.4 | 243.4 | 1.024 | 5.3 | 21 | 2736.7 |
|   | 4 | 5.2 | 98.1 | 1.012 | 39.3 | 20.7 | 814.5 |
|   | 5 | 7.0 | 60.3 | 1.006 | 0 | 5.2 | 335.3 |
| E | 1 | 6.6 | 255.2 | 1.014 | 15.1 | 10.1 | 829.8 |
|   | 4 | 7.7 | 154.5 | 1.012 | 10.2 | 7.5 | 431.6 |
|   | 5 | 8.4 | 172.5 | 1.008 | 16.4 | 17.0 | 624.3 |
| F | 1 | 5.2 | 76.1 | 1.013 | 31.2 | 0 | 1969.0 |
|   | 4 | 5.4 | 115.3 | 1.014 | 8.9 | 0 | 512.6 |
|   | 5 | 5.9 | 171.9 | 1.016 | 9.3 | 0 | 1113.8 |
| G | 1 | 7.5 | 22.9 | 1.003 | 15.4 | 5.9 | 212.8 |
|   | 4 | 6.0 | 29.8 | 1.004 | 12.3 | 0 | 193.6 |
|   | 5 | 7.4 | 23.6 | 1.003 | 6.9 | 0 | 173.2 |
| H | 1 | 5.6 | 67.5 | 1.009 | 17.9 | 11.4 | 658.8 |
|   | 4 | 6.2 | 29.6 | 1.004 | 0 | 0 | 213.7 |
|   | 5 | 5.4 | 71.6 | 1.012 | 32.1 | 24.1 | 723.2 |
| I | 1 | 6.2 | 86.8 | 1.013 | 20.0 | 12.8 | 474.6 |
|   | 4 | 6.1 | 157.9 | 1.015 | 40 | 24 | 820.2 |
|   | 5 | 6.1 | 159.9 | 1.016 | 37.1 | 23.1 | 973.7 |
| J | 1 | 6.4 | 274.3 | 1.020 | 31.5 | 25.4 | 1755.0 |
|   | 4 | 6.0 | 21.1 | 1.003 | 0 | 0 | 77.1 |
|   | 5 | 6.5 | 249.4 | 1.014 | 16.7 | 23.9 | 2238.0 |

TABLE 7-continued

Test Results from Patients Prescribed 15 mg/day Abilify ®

| Sub | Day | pH | Creatinine (mg/dL) | Specific Gravity | Aripiprazole | Dehydroaripiprazole | OPC3373 |
|---|---|---|---|---|---|---|---|
| K | 1 | 5.3 | 13.2* | 1.002* | 0 | 0 | 59.1 |
|  | 4 | 7.1 | 31.9 | 1.004 | 0 | 0 | 185.5 |
|  | 5 | 6.1 | 79.7 | 1.011 | 7.4 | 0 | 852.2 |
| L | 1 | 6.4 | 283.6 | 1.015 | 9.8 | 12.3 | 354.3 |
|  | 4 | 6.7 | 307.4 | 1.019 | 26.7 | 21.0 | 1208.1 |
|  | 5 | 5.2 | 318.2 | 1.023 | 57.3 | 33.3 | 819.6 |
| M | 1 | 5.4 | 74.0 | 1.006 | 8.9 | 6.7 | 214.4 |
|  | 4 | 6.9 | 177.4 | 1.011 | 0 | 10.1 | 842.0 |
|  | 5 | 5.1 | 67.0 | 1.006 | 12.3 | 12.3 | 292.6 |
| N | 1 | 6.8 | 7.4† | 1.001† | 0 | 0 | 0 |
|  | 4 | 6.5 | 9.8* | 1.002* | 0 | 0 | 30.3 |
|  | 5 | 6.4 | 9.6† | 1.001† | 0 | 0 | 33.8 |
| O | 1 | 6.7 | 229.7 | 1.024 | 0 | 0 | 891.5 |
|  | 4 | 7.1 | 229.9 | 1.013 | 0 | 0 | 1378.1 |
|  | 5 | 7.8 | 169.0 | 1.011 | 0 | 0 | 615.8 |
| P | 1 | 5.2 | 31.3 | 1.004 | 17.5 | 6.1 | 317.8 |
|  | 4 | 5.1 | 47.7 | 1.006 | 45.3 | 25.8 | 612.4 |
|  | 5 | 4.8 | 11.7* | 1.001* | 14.2 | 0 | 168.4 |
| Q | 1 | 5.6 | 137.9 | 1.012 | 15.0 | 5.5 | 784.0 |
|  | 4 | 5.6 | 194.5 | 1.014 | 14.5 | 8.6 | 1316.1 |
|  | 5 | 6.1 | 178.1 | 1.015 | 7.5 | 6.5 | 1126.1 |
| R | 1 | 6.8 | 92.0 | 1.013 | 10.1 | 9.6 | 997.1 |
|  | 4 | 8.5 | 17.8* | 1.003 | 6.2 | 0 | 112.4 |
|  | 5 | 5.7 | 208.5 | 1.023 | 17.7 | 24.1 | 2372.0 |
| S | 1 | 6.4 | 97.4 | 1.018 | 5.4 | 5.2 | 1182.2 |
|  | 4 | 6.8 | 86.4 | 1.019 | 5.7 | 8.1 | 1693.6 |
|  | 5 | 7.3 | 139.1 | 1.022 | 14.2 | 11.2 | 938.0 |
| T | 1 | 7.1 | 69.4 | 1.012 | 19.4 | 11.4 | 526.4 |
|  | 4 | 5.6 | 63.2 | 1.009 | 7.9 | 0 | 466.0 |
|  | 5 | 5.5 | 132.3 | 1.016 | 25.3 | 16.6 | 725.7 |
| U | 1 | 6.8 | 237.3 | 1.013 | 0 | 0 | 22.5 |
|  | 4 | 7.2 | 319.1 | 1.011 | 0 | 0 | 616.6 |
|  | 5 | 5.6 | 178.4 | 1.019 | 5.1 | 0 | 313.3 |
| V | 1 | 6.9 | 143.7 | 1.013 | 0 | 5.1 | 1086.0 |
|  | 4 | 7.6 | 98.3 | 1.010 | 0 | 0 | 559.0 |
|  | 5 | 7.6 | 114.6 | 1.011 | 0 | 0.0 | 742.6 |
| W | 1 | 6.0 | 172.6 | 1.014 | 27.6 | 14.6 | 1825.0 |
|  | 4 | 5.6 | 182.2 | 1.017 | 62.3 | 14.3 | 1805.1 |
|  | 5 | 5.3 | 138.6 | 1.015 | 76.7 | 24.9 | 1329.2 |

*Measurement is below limits for specimen validity parameter; specimen still valid.
†Invalid sample.

TABLE 8

Sample Validity and Urine Results Summary at 15 mg/day Abilify ®

|  | pH | Creatinine (mg/dL) | Specific Gravity | Aripiprazole | Dehydroaripiprazole | OPC3373 |
|---|---|---|---|---|---|---|
| Avg | 6.34 | 125.18 | 1.01 | 15.29 | 8.76 | 782.39 |
| Std Dev | 0.89 | 89.22 | 0.01 | 16.56 | 9.29 | 619.17 |
| n | 69.00 |  |  |  |  |  |
| Max | 8.50 | 319.10 | 1.03 | 76.70 | 33.30 | 2736.70 |
| Min | 4.80 | 7.40 | 1.00 | 0.00 | 0.00 | 0.00 |

Example 6

The urine of 37 patients who were prescribed 10 mg of Abilify® (aripiprazole) was tested for compliance over 5 days (Table 9). The data in Table 10 demonstrate the "normal" nature of the sample validity criteria (i.e., pH, specific gravity, and creatinine). The preponderance of OPC3373 in the urine as the major metabolic urine compound is clearly demonstrated in Table 9. Assuming 111 opportunities to determine the patient to be either positive or negative for Abilify® dosing, the use of OPC3373 resulted in 99% correct identification of those taking the prescribed medicine. Without OPC3373, only 61% were determined to be positive with patients just being below the reporting cutoffs for both aripiprazole and dehydroaripiprazole. Thus, use of OPC3373 as a urine biomarker at this dose adds value to compliance monitoring for Abilify®.

TABLE 9

Test Results from Patients Prescribed 10 mg/day Abilify ®

| Sub | Day | pH | Creatinine (mg/dL) | Specific Gravity | Aripiprazole | Dehydroaripiprazole | OPC3373 |
|---|---|---|---|---|---|---|---|
| A | 1 | 5.7 | 170.9 | 1.017 | 19.5 | 10.0 | 1936.3 |
|  | 4 | 5.8 | 124.8 | 1.016 | 7.6 | 0 | 717.3 |
|  | 5 | 5.8 | 118.1 | 1.016 | 7.6 | 0 | 1002 |
| B | 1 | 8.9 | 91.6 | 1.017 | 12.8 | 5.0 | 475.1 |
|  | 4 | 8.5 | 138.7 | 1.017 | 5.9 | 0 | 730.9 |
|  | 5 | 9.1 | 212.3 | 1.021 | 18.6 | 8.8 | 1965.3 |
| C | 1 | 6.1 | 345.1 | 1.029 | 16.0 | 23.7 | 1555.6 |
|  | 4 | 6.5 | 170.7 | 1.016 | 5.0 | 7.0 | 639.5 |
|  | 5 | 7.0 | 80.9 | 1.008 | 0 | 6.6 | 259.6 |
| D | 1 | 5.6 | 147.2 | 1.015 | 14.9 | 0 | 731.9 |
|  | 4 | 5.8 | 169.2 | 1.016 | 8.7 | 0 | 1508.1 |
|  | 5 | 6.6 | 215.2 | 1.015 | 7.6 | 0 | 2397.6 |
| E | 1 | 6.8 | 90.4 | 1.013 | 0 | 0 | 86.6 |
|  | 4 | 7.3 | 117.5 | 1.014 | 0 | 0 | 115 |
|  | 5 | 7.8 | 126.9 | 1.006 | 0 | 0 | 163.8 |
| F | 1 | 6.5 | 45.1 | 1.005 | 0 | 0 | 155.9 |
|  | 4 | 5.5 | 44.2 | 1.004 | 4.6 | 0 | 147.9 |
|  | 5 | 5.1 | 45.0 | 1.005 | 0.0 | 0 | 169.8 |
| G | 1 | 5.1 | 93.2 | 1.011 | 23.7 | 13.0 | 900.6 |
|  | 4 | 5.0 | 217.7 | 1.013 | 39.0 | 16.9 | 2569.1 |
|  | 5 | 5.1 | 97.6 | 1.009 | 26.2 | 8.0 | 1089.0 |
| H | 1 | 5.6 | 162.4 | 1.018 | 58.2 | 14 | 2792.7 |
|  | 4 | 5.8 | 112.7 | 1.009 | 13.8 | 0.0 | 1363.5 |
|  | 5 | 6.1 | 73.5 | 1.004 | 10.2 | 0 | 662.9 |
| I | 1 | 5.6 | 162.4 | 1.018 | 58.2 | 14 | 2792.7 |
|  | 4 | 6.1 | 105.8 | 1.009 | 0 | 5.0 | 726.0 |
|  | 5 | 6.0 | 150.9 | 1.011 | 7.3 | 7.7 | 1402.4 |
| J | 1 | 5.6 | 241.8 | 1.015 | 15.8 | 14.3 | 2443.3 |
|  | 4 | 6.3 | 184.5 | 1.014 | 0 | 0 | 555.7 |
|  | 5 | 5.2 | 167.9 | 1.013 | 14.2 | 12.2 | 540.4 |
| K | 1 | 5.9 | 189.3 | 1.013 | 11.6 | 0 | 686.6 |
|  | 4 | 7.9 | 165.7 | 1.010 | 0 | 0 | 165.6 |
|  | 5 | 8.3 | 182.6 | 1.010 | 0 | 0 | 351.4 |
| L | 1 | 8.6 | 35.5 | 1.007 | 0 | 0 | 42.3 |
|  | 4 | 5.2 | 86.9 | 1.006 | 11.7 | 5.4 | 310.2 |
|  | 5 | 5.1 | 26.4 | 1.003 | 7.6 | 0 | 70.1 |
| M | 1 | 6.3 | 60.5 | 1.004 | 0 | 0 | 187.9 |
|  | 4 | 5.4 | 182.0 | 1.019 | 0 | 0 | 0 |
|  | 5 | 6.5 | 156.7 | 1.016 | 0 | 0 | 469.6 |
| N | 1 | 5.6 | 152.0 | 1.016 | 16.2 | 0 | 647.3 |
|  | 4 | 4.9 | 10.0* | 1.002* | 6.3 | 0 | 213.9 |
|  | 5 | 5.2 | 239.8 | 1.019 | 52.0 | 59.3 | 1179.8 |
| O | 1 | 5.5 | 204.1 | 1.017 | 19.8 | 20.3 | 1033.6 |
|  | 4 | 5.9 | 257.0 | 1.016 | 6.5 | 20.7 | 685.5 |
|  | 5 | 6.8 | 161.0 | 1.014 | 0 | 5.5 | 395.7 |
| P | 1 | 5.7 | 370.2 | 1.020 | 20.9 | 22.0 | 907.7 |
|  | 4 | 6.9 | 148.2 | 1.010 | 0.0 | 0.0 | 253.6 |
|  | 5 | 6.7 | 127.9 | 1.010 | 0 | 0 | 267.9 |
| Q | 1 | 6.5 | 212.8 | 1.012 | 0 | 0 | 738.6 |
|  | 4 | 7.2 | 77.4 | 1.008 | 0 | 0 | 1053.4 |
|  | 5 | 7.1 | 101.9 | 1.007 | 0 | 0 | 1286.9 |
| R | 1 | 7.1 | 50.9 | 1.006 | 0 | 0 | 536.8 |
|  | 4 | 6.9 | 32.4 | 1.003 | 0 | 0 | 78.9 |
|  | 5 | 7.8 | 193.4 | 1.011 | 6.2 | 0 | 813.9 |
| S | 1 | 7.6 | 156.0 | 1.005 | 0 | 0 | 532.4 |
|  | 4 | 5.9 | 33.7 | 1.003 | 14.2 | 0 | 124.9 |
|  | 5 | 5.8 | 58.0 | 1.005 | 21.3 | 0 | 221.6 |
| T | 1 | 6.0 | 101.3 | 1.007 | 33.1 | 6.7 | 439.6 |
|  | 4 | 6.8 | 114.4 | 1.010 | 0 | 0 | 204.0 |
|  | 5 | 6.8 | 196.2 | 1.011 | 5.9 | 8.0 | 449.1 |
| U | 1 | 5.9 | 36.8 | 1.004 | 0 | 0 | 56.0 |
|  | 4 | 6.5 | 118.9 | 1.011 | 0 | 0 | 156.1 |
|  | 5 | 6.7 | 143.7 | 1.007 | 0 | 0 | 275.8 |
| V | 1 | 5.7 | 378.9 | 1.017 | 5.6 | 9.4 | 280.5 |
|  | 4 | 5.1 | 248.0 | 1.021 | 102.7 | 64.8 | 4601.6 |

TABLE 9-continued

Test Results from Patients Prescribed 10 mg/day Abilify ®

| Sub | Day | pH | Creat-inine (mg/dL) | Specific Gravity | Aripip-razole | Dehydro-aripip-razole | OPC3373 |
|---|---|---|---|---|---|---|---|
|   | 5 | 5.9 | 18.8* | 1.002* | 7.1 | 0 | 227.4 |
| W | 1 | 6.4 | 10.3* | 1.001† | 9.5 | 0 | 137.0 |
|   | 4 | 7.2 | 60.0 | 1.008 | 0 | 0 | 260.7 |
|   | 5 | 6.4 | 9.3* | 1.001 | 0 | 0 | 40.9 |
| X | 1 | 9.3 | 87.0 | 0.999 | 0 | 0 | 966.1 |
|   | 4 | 5.8 | 131.8 | 1.011 | 19.6 | 12.2 | 762.2 |
|   | 5 | 5.7 | 163.7 | 1.014 | 15.6 | 8.3 | 762.1 |
| Y | 1 | 5.9 | 248.5 | 1.020 | 28.2 | 17.2 | 1429.0 |
|   | 4 | 5.9 | 99.6 | 1.009 | 6.1 | 0 | 201.9 |
|   | 5 | 6.9 | 37.3 | 1.002* | 0 | 0 | 135.1 |
| Z | 1 | 7.3 | 48.5 | 1.003 | 0 | 0 | 119.1 |
|   | 4 | 6.8 | 31.6 | 1.007 | 0 | 0 | 173.1 |
|   | 5 | 5.0 | 47.8 | 1.011 | 13.8 | 0 | 375.3 |
| AA | 1 | 6.6 | 27.5 | 1.006 | 0 | 0 | 238.4 |
|   | 4 | 6.5 | 144.8 | 1.011 | 0 | 0 | 255.3 |
|   | 5 | 7.0 | 88.6 | 1.008 | 0 | 0 | 105.5 |
| BB | 1 | 6.7 | 232.3 | 1.009 | 0 | 0 | 231.5 |
|   | 4 | 6.4 | 177.4 | 1.015 | 9.7 | 5.0 | 1640.0 |
|   | 5 | 6.6 | 158.6 | 1.014 | 0 | 0 | 1541.0 |
| CC | 1 | 5.3 | 230.2 | 1.017 | 30.9 | 9.8 | 1945.9 |
|   | 4 | 6.8 | 60.3 | 1.006 | 0.0 | 0.0 | 166.4 |
|   | 5 | 6.3 | 51.9 | 1.009 | 0 | 0 | 128.8 |
| DD | 1 | 5.6 | 20.4 | 1.006 | 0 | 0 | 67.3 |
|   | 4 | 5.8 | 130.3 | 1.012 | 28.4 | 24.6 | 2307.7 |
|   | 5 | 6.2 | 29.5 | 1.002 | 0 | 5.9 | 339.3 |
| EE | 1 | 6.3 | 59.7 | 1.006 | 0 | 0 | 132.5 |
|   | 4 | 5.4 | 111.9 | 1.014 | 19.5 | 10.7 | 1090.7 |
|   | 5 | 5.7 | 82.3 | 1.012 | 18.2 | 10.5 | 750 |
| FF | 1 | 5.6 | 82.0 | 1.011 | 19.5 | 11.2 | 740.4 |
|   | 4 | 5.1 | 208.5 | 1.018 | 19.3 | 21.9 | 508.3 |
|   | 5 | 4.9 | 212.2 | 1.022 | 29.2 | 25.6 | 663.3 |
| GG | 1 | 6.7 | 139.5 | 1.012 | 7.5 | 7.9 | 408.0 |
|   | 4 | 5.2 | 18.2* | 1.008 | 74.2 | 31.6 | 77.2 |
|   | 5 | 4.7 | 26.0 | 1.009 | 71.0 | 30.3 | 89.2 |
| HH | 1 | 6.8 | 267.2 | 1.017 | 28.7 | 37.6 | 2418.1 |
|   | 4 | 5.9 | 33.0 | 1.004 | 11.2 | 3.1 | 221.1 |
|   | 5 | 5.7 | 43.8 | 1.006 | 10.4 | 5.9 | 406.5 |
| II | 1 | 5.6 | 20.7 | 1.003 | 5.5 | 0 | 118.0 |
|   | 4 | 6.5 | 116.6 | 1.011 | 0 | 0 | 455.5 |
|   | 5 | 6.3 | 183.6 | 1.014 | 9.4 | 11.6 | 698.4 |
| JJ | 1 | 7.0 | 101.6 | 1.013 | 0 | 0 | 454.8 |
|   | 4 | 7.4 | 101.2 | 1.009 | 0 | 0 | 145.0 |
|   | 5 | 5.4 | 131.2 | 1.008 | 8.3 | 0 | 257.9 |
| KK | 1 | 6.1 | 158.2 | 1.010 | 0 | 0 | 324.2 |
|   | 4 | 5.5 | 209.4 | 1.019 | 30.3 | 5.6 | 1467.6 |
|   | 5 | 5.7 | 176.9 | 1.019 | 27.1 | 12.1 | 1446.5 |

*Measurement is below limits for specimen validity parameter; specimen still valid.
†Invalid sample.

TABLE 10

Sample Validity and Urine Results Summary at 10 mg/day Abilify ®

|   | pH | Creat-inine (mg/dL) | Specific Gravity | Aripip-razole | Dehydro-aripip-razole | OPC3373 |
|---|---|---|---|---|---|---|
| avg | 6.27 | 126.71 | 1.01 | 11.67 | 6.27 | 718.43 |
| std dev | 0.94 | 78.55 | 0.01 | 17.32 | 11.13 | 770.47 |
| n | 111 |   |   |   |   |   |
| Max | 9.3 | 378.9 | 1.029 | 102.7 | 64.8 | 4601.6 |
| Min | 4.7 | 9.3 | 0.999 | 0 | 0 | 0 |

Example 7

The urine of 25 patients who were prescribed 5 mg of Abilify® (aripiprazole) was tested for compliance over 5 days (Table 11). The data in Table 12 demonstrate the "normal" nature of the sample validity criteria (i.e., pH, specific gravity, and creatinine). The preponderance of OPC3373 in the urine as the major metabolic urine compound is clearly demonstrated in Table 11. Assuming 75 opportunities to determine the patient to be either positive or negative for Abilify® dosing, the use of OPC3373 resulted in 99% correct identification of those taking the prescribed medicine. Without OPC3373, only 47% were determined to be positive with patients just being below the reporting cutoffs for both aripiprazole and dehydroaripiprazole. Thus, use of OPC3373 as a urine biomarker at this lower dose adds a great deal of value to compliance monitoring for Abilify®.

TABLE 11

Test Results from Patients Prescribed 5 mg/day Abilify ®

| Sub | Day | pH | Creat-inine (mg/dL) | Specific Gravity | Aripip-razole | Dehydro-aripip-razole | OPC3373 |
|---|---|---|---|---|---|---|---|
| A | 1 | 5.3 | 45.2 | 1.006 | 5.4 | 0 | 80.0 |
|   | 4 | 7.6 | 147.5 | 1.010 | 11.8 | 0 | 363.1 |
|   | 5 | 8.7 | 204.2 | 1.001† | 31.6 | 15.1 | 1053.3 |
| B | 1 | 5.2 | 84.1 | 1.010 | 10.1 | 6.6 | 139.6 |
|   | 4 | 4.9 | 103.5 | 1.010 | 21.5 | 10.2 | 130.4 |
|   | 5 | 5.1 | 99.2 | 1.009 | 10.2 | 5.7 | 152.7 |
| C | 1 | 7.2 | 94.9 | 1.013 | 0 | 0 | 148.7 |
|   | 4 | 5.6 | 166.2 | 1.020 | 11.3 | 0 | 377.0 |
|   | 5 | 8.3 | 121.2 | 1.006 | 5.1 | 0 | 531.4 |
| D | 1 | 5.4 | 203.4 | 1.016 | 9 | 0 | 972.3 |
|   | 4 | 5.4 | 129.1 | 1.014 | 6.6 | 0 | 520.3 |
|   | 5 | 5.2 | 155.4 | 1.017 | 7.3 | 0 | 233.0 |
| E | 1 | 7.0 | 12.9* | 1.003 | 0 | 0 | 32.8 |
|   | 4 | 6.7 | 15.8* | 1.003 | 0.0 | 0 | 39.6 |
|   | 5 | 6.8 | 23.1 | 1.004 | 0 | 0 | 59.1 |
| F | 1 | 6.6 | 61.0 | 1.006 | 0 | 0 | 355.1 |
|   | 4 | 6.0 | 63.4 | 1.005 | 5.2 | 0 | 695.3 |
|   | 5 | 6.9 | 43.0 | 1.004 | 0 | 0 | 218.3 |
| G | 1 | 6.8 | 26.8 | 1.005 | 0 | 0 | 75.0 |
|   | 4 | 6.8 | 30.2 | 1.004 | 0 | 0 | 107.5 |
|   | 5 | 6.4 | 36.4 | 1.005 | 0 | 0 | 92.1 |
| H | 1 | 7.6 | 149.5 | 1.008 | 0 | 0 | 179.9 |
|   | 4 | 7.8 | 137.1 | 1.007 | 0 | 0 | 333.6 |
|   | 5 | 8.9 | 151.3 | 1.000* | 14.9 | 5.2 | 438.5 |
| I | 1 | 4.9 | 57.8 | 1.005 | 7.5 | 0 | 69.8 |
|   | 4 | 7.3 | 129.7 | 1.004 | 0 | 0 | 347.1 |
|   | 5 | 7.5 | 104.7 | 1.005 | 0 | 0 | 208.0 |
| J | 1 | 7.3 | 244.5 | 1.012 | 0 | 0 | 1123.5 |
|   | 4 | 7.8 | 283.2 | 1.011 | 0 | 0 | 673.9 |
|   | 5 | 7.0 | 205.3 | 1.013 | 0 | 0 | 422.2 |
| K | 1 | 7.0 | 55.5 | 1.004 | 0 | 0 | 36.1 |
|   | 4 | 7.1 | 39.8 | 1.003 | 0 | 0 | 18.1 |
|   | 5 | 6.9 | 29.6 | 1.002 | 0.0 | 0 | 29.1 |
| L | 1 | 5.5 | 88.1 | 1.014 | 5.0 | 0 | 250.5 |
|   | 4 | 5.3 | 163.5 | 1.014 | 32.4 | 17.1 | 643.5 |
|   | 5 | 6.0 | 165.2 | 1.012 | 5.3 | 5.5 | 528.1 |
| M | 1 | 5.9 | 64.3 | 1.008 | 0 | 0 | 211.7 |
|   | 4 | 5.6 | 106.6 | 1.014 | 0.0 | 0 | 293.9 |
|   | 5 | 7.4 | 22.3 | 1.002* | 0 | 0 | 31.8 |
| N | 1 | 5.6 | 226.8 | 1.030 | 9.7 | 0 | 1277.8 |
|   | 4 | 8.3 | 83.6 | 1.016 | 13.1 | 0 | 359.8 |
|   | 5 | 5.9 | 126.4 | 1.023 | 0 | 0 | 492.7 |
| O | 1 | 6.1 | 45.4 | 1.010 | 8.5 | 0 | 197.2 |
|   | 4 | 5.1 | 79.4 | 1.013 | 15.6 | 8.0 | 306.3 |
|   | 5 | 6.3 | 46.7 | 1.008 | 0 | 0 | 169.9 |
| P | 1 | 6.5 | 135.1 | 1.011 | 8.8 | 5.1 | 941.3 |
|   | 4 | 6.6 | 153.9 | 1.011 | 6.5 | 0 | 1125.4 |
|   | 5 | 7.2 | 130.5 | 1.010 | 0 | 0 | 816.9 |
| Q | 1 | 5.2 | 138.9 | 1.015 | 8.4 | 7.4 | 194.7 |
|   | 4 | 6.5 | 50.5 | 1.008 | 0 | 0 | 32.8 |
|   | 5 | 6.5 | 41.1 | 1.007 | 0 | 0 | 28.5 |
| R | 1 | 5.6 | 15.3* | 1.001† | 0 | 0 | 65.2 |
|   | 4 | 5.9 | 41.6 | 1.003 | 0 | 0 | 150.5 |
|   | 5 | 5.1 | 58.2 | 1.005 | 0 | 0 | 214.5 |
| S | 1 | 5.2 | 75.2 | 1.008 | 13.1 | 0 | 200.2 |
|   | 4 | 5.4 | 42.9 | 1.007 | 10.3 | 0 | 148.4 |
|   | 5 | 5.5 | 65.4 | 1.009 | 10.1 | 0 | 214.5 |
|   | 1 | 5.4 | 307.9 | 1.017 | 6.4 | 5.3 | 1015.6 |

TABLE 11-continued

Test Results from Patients Prescribed 5 mg/day Abilify ®

| Sub | Day | pH | Creatinine (mg/dL) | Specific Gravity | Aripiprazole | Dehydroaripiprazole | OPC3373 |
|---|---|---|---|---|---|---|---|
| T | 4 | 7.3 | 266.3 | 1.013 | 7.5 | 7.5 | 329.5 |
|   | 5 | 9.1* | 269.1 | 1.028 | 0 | 15.8 | 538.0 |
|   | 1 | 6.0 | 139.6 | 1.016 | 0 | 0 | 174.2 |
| U | 4 | 5.3 | 179.2 | 1.016 | 6.6 | 7.4 | 162.5 |
|   | 5 | 6.1 | 146.0 | 1.014 | 0 | 0 | 272.3 |
|   | 1 | 8.4 | 80.3 | 1.003 | 0 | 0 | 112.3 |
| V | 4 | 7.8 | 23.1 | 1.003 | 0 | 0 | 29.7 |
|   | 5 | 9.0 | 40.5 | 0.999† | 0 | 0 | 121.7 |
|   | 1 | 6.0 | 121.0 | 1.009 | 0 | 0 | 130.8 |
| W | 4 | 5.5 | 155.1 | 1.010 | 5.5 | 8.4 | 253.1 |
|   | 5 | 5.9 | 289.5 | 1.017 | 12.7 | 8.2 | 496.9 |
|   | 1 | 4.9 | 163.6 | 1.016 | 38.4 | 8.7 | 476.5 |
| X | 4 | 4.9 | 39.2 | 1.003 | 9.5 | 0 | 57.2 |
|   | 5 | 5.6 | 162.0 | 1.013 | 9.7 | 0 | 385.0 |
|   | 1 | 5.0 | 110.8 | 1.008 | 0 | 0 | 61.0 |
| Y | 4 | 5.2 | 82.9 | 1.005 | 0 | 0 | 31.0 |
|   | 5 | 5.0 | 139.3 | 1.010 | 0 | 0 | 57.4 |

*Measurement is below limits for specimen validity parameter; specimen still valid.
†Invalid sample.

TABLE 12

Sample Validity and Urine Results Summary at 5 mg/day Abilify ®

|  | pH | Creatinine (mg/dL) | Specific Gravity | Aripiprazole | Dehydroaripiprazole | OPC3373 |
|---|---|---|---|---|---|---|
| Avg | 6.37 | 111.16 | 1.01 | 5.34 | 1.96 | 318.10 |
| Std Dev | 1.13 | 72.96 | 0.01 | 7.87 | 4.05 | 305.90 |
| n | 75 |  |  |  |  |  |
| Max | 9.1 | 307.9 | 1.03 | 38.4 | 17.1 | 1277.8 |
| Min | 4.9 | 12.9 | 0.999 | 0 | 0 | 18.1 |

TABLE 13

Urine drug/metabolite concentrations on Days 1, 4 and 5 at 5 mg/day Abilify ®

|  |  | Aripiprazole | Dehydroaripiprazole | OPC3373 |
|---|---|---|---|---|
| Day 1 | N (%) Positive | 4 (80%) | 2 (40%) | 4 (80%) |
|  | Mean +/− SD | 12.4 +/− 8.8 | 2.3 +/− 3.2 | 375.7 +/− 493.1 |
|  | Median | 11.1 | 0 | 175 |
|  | Extremes | 0-22.3 | 0-6.5 | 0-1214 |
| Day 4 | N (%) Positive | 2 (40%) | 1 (20%) | 4 (80%) |
|  | Mean +/− SD | 5.8 +/− 8.0 | 1.2 +/− 2/7 | 245.3 +/− 16.5 |
|  | Median | 0 | 0 | 228.2 |
|  | Extremes | 0-16.3 | 0-6.1 | 0-571.4 |
| Day 5 | N (%) Positive | 2 (40%) | 1 (20%) | 4 (80%) |
|  | Mean +/− SD | 6.1 +/− 9.2 | 1.6 +/− 3/7 | 216.8 +/− 92.9 |
|  | Median | 0 | 0 | 182.4 |
|  | Extremes | 0-18.3 | 0-8.2 | 0-493.9 |

Example 8

The urine of 15 patients who were prescribed 2 mg of Abilify® (aripiprazole) was tested for compliance over 5 days (Table 14). The data in Table 14 demonstrate the "normal" nature of the sample validity criteria (i.e., pH, specific gravity, and creatinine). The preponderance of OPC3373 in the urine as the major metabolic urine compound is clearly demonstrated in Table 14. Assuming 45 opportunities to determine the patient to be either positive or negative for Abilify® dosing, the use of OPC3373 resulted in 87% correct identification of those taking the prescribed medicine. Without OPC3373, only 24% were determined to be positive with patients just being below the reporting cutoffs for both aripiprazole and dehydroaripiprazole. Thus, use of OPC3373 as a urine biomarker at this lower dose makes compliance monitoring for Abilify® possible. Two patients in Table 14 demonstrated very low levels of creatinine and as is well known in the industry may have been severely diluted such that in one subject (subject K), the aripiprazole metabolite, OPC3373, was below levels of quantitation for all samples collected. However, OPC3373 in subject M confirmed the subject's adherence to aripiprazole therapy despite the low observed creatinine level.

TABLE 14

Test Results from Patients Prescribed 2 mg/day Abilify ®

| Sub | Day | pH | Creatinine (mg/dL) | Specific Gravity | Aripiprazole | Dehydroaripiprazole | OPC3373 |
|---|---|---|---|---|---|---|---|
| A | 1 | 6.7 | 175.7 | 1.025 | 0 | 0 | 196.1 |
|   | 4 | 8.0 | 260.4 | 1.028 | 0.0 | 0 | 451.1 |
|   | 5 | 5.8 | 314.4 | 1.029 | 0 | 0 | 478.7 |
| B | 1 | 5.3 | 180.5 | 1.023 | 9.0 | 0 | 174.1 |
|   | 4 | 5.7 | 108.9 | 1.010 | 0 | 0 | 76.5 |
|   | 5 | 8.9 | 159.8 | 1.024 | 10.5 | 0 | 243.0 |
| C | 1 | 6.6 | 61.2 | 1.008 | 0 | 0 | 159.2 |
|   | 4 | 5.9 | 48.4 | 1.005 | 0 | 0 | 113.0 |
|   | 5 | 6.3 | 39.4 | 1.003 | 0 | 0 | 85.4 |
| D | 1 | 5.2 | 170.5 | 1.022 | 7.9 | 0 | 166.8 |
|   | 4 | 6.9 | 53.1 | 1.016 | 0 | 0 | 194.9 |
|   | 5 | 8.6 | 107.8 | 1.004 | 30.9 | 10.7 | 715.8 |
| E | 1 | 7.0 | 31.2 | 1.007 | 0 | 0 | 0 |
|   | 4 | 6.8 | 22.2 | 1.005 | 0 | 0 | 0 |
|   | 5 | 7.9 | 25.1 | 1.003 | 0 | 0 | 0 |
| F | 1 | 5.4 | 112.0 | 1.015 | 0 | 0 | 57.0 |
|   | 4 | 7.0 | 195.2 | 1.014 | 0 | 0 | 226.2 |
|   | 5 | 5.6 | 182.8 | 1.017 | 0 | 0 | 257.1 |
| G | 1 | 6.7 | 49.7 | 1.005 | 0 | 0 | 37.7 |
|   | 4 | 8.6 | 41.2 | 0.998 | 0 | 0 | 84.8 |
|   | 5 | 8.8 | 48.4 | 0.997 | 0 | 0 | 109.7 |
| H | 1 | 6.3 | 80.6 | 1.014 | 0 | 0 | 156.3 |
|   | 4 | 5.8 | 84.5 | 1.007 | 0 | 0 | 211.1 |
|   | 5 | 6.0 | 174.6 | 1.019 | 6.1 | 0.0 | 372.3 |
| I | 1 | 6.2 | 42.0 | 1.006 | 0 | 0 | 40.4 |
|   | 4 | 5.4 | 116.2 | 1.011 | 0 | 0 | 250.8 |
|   | 5 | 6.5 | 275.5 | 1.017 | 0 | 0 | 460.4 |
| J | 1 | 5.5 | 228.6 | 1.014 | 0 | 0 | 132.3 |
|   | 4 | 5.2 | 152.9 | 1.011 | 0 | 0 | 40.5 |
|   | 5 | 5.1 | 153.4 | 1.014 | 6.0 | 0 | 47.0 |
| K | 1 | 6.2 | 22.4 | 1.003 | 0 | 0 | 0.0 |
|   | 4 | 7.0 | 17.6* | 1.004 | 0 | 0 | 0 |
|   | 5 | 5.7 | 27.0 | 1.005 | 0 | 0 | 0 |
| L | 1 | 5.2 | 169.4 | 1.015 | 0 | 0 | 103.1 |
|   | 4 | 5.3 | 78.3 | 1.010 | 0 | 0 | 54.9 |
|   | 5 | 6.0 | 286.7 | 1.014 | 0 | 0 | 328.2 |
| M | 1 | 5.9 | 41.9 | 1.006 | 0 | 0 | 43.0 |
|   | 4 | 6.8 | 17.9* | 1.002* | 0 | 0 | 31.0 |
|   | 5 | 5.8 | 96.8 | 1.012 | 11.2 | 0 | 198.2 |
| N | 1 | 5.4 | 172.2 | 1.018 | 0 | 0 | 240.4 |
|   | 4 | 7 | 63.6 | 1.010 | 0 | 0 | 79.7 |
|   | 5 | 6.1 | 140.9 | 1.011 | 0 | 0 | 144.7 |
| O | 1 | 5.3 | 77.6 | 1.008 | 0 | 0 | 104.9 |
|   | 4 | 4.7 | 42.1 | 1.005 | 0 | 0 | 49.4 |
|   | 5 | 6.5 | 117.7 | 1.013 | 0 | 0 | 176.0 |

*Measurement is below limits for specimen validity parameter; specimen still valid.

TABLE 15

Sample Validity and Urine Results Summary at 2 mg/day Abilify ®

|  | pH | Creatinine (mg/dL) | Specific Gravity | Aripiprazole | Dehydroaripiprazole | OPC3373 |
|---|---|---|---|---|---|---|
| Avg | 6.32 | 112.63 | 1.01 | 1.81 | 0.24 | 157.59 |
| Std Dev | 1.05 | 79.79 | 0.01 | 5.35 | 1.60 | 151.65 |
| n | 45 | | | | | |
| Max | 8.9 | 314.4 | 1.029 | 30.9 | 10.7 | 715.8 |
| Min | 4.7 | 17.6 | 0.997 | 0 | 0 | 0 |

TABLE 16

Urine drug/metabolite concentrations on Days 1, 4 and 5 at 2 mg/day Abilify ®

|  |  | Aripiprazole | Dehydroaripiprazole | OPC3373 |
|---|---|---|---|---|
| Day 1 | N (%) Positive | 8 (53%) | 1 (7%) | 15 (100%) |
|  | Mean +/− SD | 5.1 +/− 5.7 | 0.5 +/− 1.9 | 186.1 +/− 183.8 |
|  | Median | 5.8 | 0 | 122.2 |
|  | Extremes | 0-17.4 | 0-7.4 | 63.6-649.8 |
| Day 4 | N (%) Positive | 8 (53%) | 0 (0%) | 15 (100%) |
|  | Mean +/− SD | 5.0 +/− 5.9 | 0 +/− 0 | 248.6 +/− 195.1 |
|  | Median | 5.8 | 0 | 197.1 |
|  | Extremes | 0-18.3 | 0-0 | 55-820.5 |
| Day 5 | N (%) Positive | 7 (47%) | 0 (0%) | 14 (93%) |
|  | Mean +/− SD | 4.1 +/− 4.9 | 0 +/− 0 | 194.9 +/− 235.2 |
|  | Median | 0 | 0 | 182.4 |
|  | Extremes | 0-12.8 | 0-0 | 0-493.9 |

Thus, in separate populations (e.g., different dose groups), the use of OPC3373 to monitor patient adherence is more sensitive than using the more commonly available and predicted compounds aripiprazole and dehydroaripiprazole. Indeed, without using OPC3373, 5 out of 22 patients in the first study and 1 out of 6 patients in the second study would have been incorrectly identified as "negative" while at a dosage of 2 mg/day, only 24% of the patients would be correctly identified as taking their medicine.

What is claimed is:

1. A method for recommending a modification to an aripiprazole therapy, the method comprising:
   identifying a subject who is prescribed aripiprazole therapy;
   determining a prescribed aripiprazole dose associated with the prescribed aripiprazole therapy;
   measuring a concentration of OPC3373 and a creatinine level in urine of the subject;
   normalizing the concentration of OPC3373 as a function of the creatinine level;
   identifying the subject as non-adherent to aripiprazole therapy if the normalized concentration of OPC3373 is less than a predetermined level, and as adherent to aripirazole therapy if the normalized concentration of OPC3373 is greater than the predetermined level; and
   recommending a modification to the prescribed aripiprazole dose if the subject is identified as non-adherent, wherein the modification comprises a discontinuation of the aripiprazole therapy or a replacement of the aripiprazole therapy with a new therapeutic regimen.

2. The method of claim 1 further comprising counseling the subject on dangers of non-adherence to aripiprazole therapy if the subject is identified as non-adherent.

3. The method of claim 1, wherein the predetermined level is 25 ng/mL.

4. The method of claim 1, wherein the aripiprazole therapy comprises prescribing to the subject aripiprazole in an amount selected from the group consisting of: 2 mg/day, 5 mg/day, 10 mg/day, 15 mg/day, 20 mg/day, or 30 mg/day.

5. The method of claim 1, wherein the concentration of OPC3373 is measured by LC/MSMS.

6. The method of claim 1, wherein the concentration of OPC3373 is measured by LC/MS(TOF).

7. The method of claim 1, wherein the concentration of OPC3373 is measured by direct administration to a mass spectrometer.

8. The method of claim 7, wherein the direct administration comprises Rapidfire or laser diode thermal desorption ("LDTD").

9. The method of claim 1 further comprising:
   measuring a concentration of aripiprazole in urine of the subject, wherein the subject is identified as non-adherent if the concentrations of aripiprazole and OPC3373 are both less than predetermined levels of aripiprazole and OPC3373, respectively.

10. The method of claim 9, wherein the predetermined level of aripiprazole is 5 ng/mL.

11. The method of claim 9, wherein the predetermined level of OPC3373 is 25 ng/mL.

12. The method of claim 9 further comprising:
   measuring a concentration of dehydroaripiprazole in urine of the subject, wherein the subject is identified as non-adherent if the concentration aripiprazole, dehydroaripiprazole and OPC3373 are each less than predetermined levels of aripiprazole, dehydroaripiprazole and OP3173, respectively.

13. The method of claim 12, wherein the predetermined level of dehydroaripprazole is 5 ng/mL.

14. The method of claim 12, wherein the predetermined level of aripiprazole is 5 ng/mL.

15. The method of claim 12, the predetermined level of OPC3373 is 25 ng/mL.

16. The method of claim 12, wherein the concentration of OPC3373 is measured by LC/MSMS.

17. The method of claim 1 further comprising:
   measuring a concentration of dehydroaripiprazole in urine of the subject, wherein the subject is identified as non-adherent if the concentrations of dehydroaripiprazole and OPC3373 are both less than predetermined levels of dehydroaripiprazole and OPC3373, respectively.

18. The method of claim 17, wherein the predetermined level of dehydroaripiprazole is 5 ng/mL.

19. The method of claim 17, wherein the predetermined level of OPC3373 is 25 ng/mL.

20. The method of claim 17, wherein the concentration of OPC3373 is measured by LC/MSMS.

21. The method of claim 1 wherein the predetermined level comprises a ratio of the OPC3373 concentration to the creatinine level.

22. The method of claim 21 further comprising:
   measuring an aripiprazole concentration in urine of the subject and optionally a specific gravity value; and
   normalizing the aripiprazole concentration as a function of the creatinine level and/or the specific gravity value,
   wherein the predetermined level comprises a ratio of the normalized OPC3373 concentration and/or the aripiprazole concentration to the creatinine level and/or the specific gravity value.

23. The method of claim 21 further comprising:
measuring a dehydroaripiprazole concentration in urine of the subject; and
normalizing the dehydroaripiprazole concentration as a function of the creatinine level and/or a specific gravity value,
wherein the predetermined level comprises a ratio of the dehydroaripiprazole concentration to the creatinine level and/or the specific gravity value.

24. The method of claim 1 further comprising:
generating a normal distribution of OPC3373 in aripiprazole subjects using a log of a plurality of normalized OPC3373 concentrations in urine of a plurality of subjects who have received aripiprazole therapy and are known to have been adherent.

25. The method of claim 24 further comprising:
identifying a normalized concentration of OPC3373 in urine of the subject as normal if it falls within the normal distribution of OPC3373 in aripiprazole subjects; and/or
identifying the normalized concentration of OPC3373 in urine of the subject as not normal if it falls outside the normal distribution of OPC3373 in aripiprazole subjects.

26. The method of claim 25, further comprising generating a second, refined normal distribution of OPC3373 in aripiprazole subjects using the normalized OPC3373 concentration in urine of the subject if it is identified as normal.

27. The method of claim 1 further comprising:
measuring an aripiprazole concentration in urine of each of a plurality of aripiprazole subjects known to be adherent; and
generating a normal distribution of aripirazole in aripiprazole subjects using a log of a plurality of aripiprazole concentrations in urine of the plurality of subjects.

28. The method of claim 27 further comprising:
measuring an aripiprazole concentration in the subject; and
identifying the aripiprazole concentration in urine of the subject; as normal if it falls within the normal distribution of aripiprazole in aripiprazole subjects; and/or
identifying the aripiprazole concentration in urine of the subject as not normal if it falls outside the normal distribution of aripiprazole in aripiprazole subjects.

29. The method of claim 28 further comprising generating a second, refined normal distribution of aripiprazole in aripiprazole subjects using the aripiprazole concentration in urine of the subject if it is identified as normal.

30. The method of claim 1 further comprising:
measuring a dehydroaripiprazole concentration in urine of each of a plurality of aripiprazole subjects known to be adherent; and
generating a normal distribution of dehydroaripiprazole inaripiprazole subjects using a log of the dehydroaripiprazole concentrations in urine of the plurality of aripiprazole subjects.

31. The method of claim 30 further comprising:
measuring a dehydroaripiprazole concentration in the subject; and
identifying the dehydroaripiprazole concentration as normal if it falls within the normal distribution of dehydroaripiprazole in aripiprazole subjects; and/or
identifying the dehydroaripiprazole concentration as not normal if it falls outside the normal distribution of dehydroaripiprazole in aripiprazole subjects.

32. The method of claim 31 further comprising generating a second, refined normal distribution of dehydroaripiprazole in aripiprazole subjects using the dehydroaripiprazole concentration of the subject if it is identified as normal.

33. The method of claim 1 further comprising recommending maintaining the prescribed aripiprazole dose if the subject is identified as adherent.

34. The method of claim 33, wherein the step of recommending maintaining the prescribed aripiprazole dose comprises recommending no modification to the prescribed aripiprazole dose.

35. The method of claim 33, wherein the step of recommending maintaining the prescribed aripiprazole dose comprises recommending no significant modification to the prescribed aripiprazole dose.

* * * * *